United States Patent
Walter

(10) Patent No.: US 6,441,169 B1
(45) Date of Patent: Aug. 27, 2002

(54) PYRIMIDIN-2-OXY-4-ONE AND PYRIMIDIN-2-OXY-4-THIONE DERIVATIVES

(75) Inventor: Harald Walter, Rodersdorf (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/486,852

(22) PCT Filed: Sep. 2, 1998

(86) PCT No.: PCT/EP98/05572

§ 371 (c)(1), (2), (4) Date: Mar. 3, 2000

(87) PCT Pub. No.: WO99/11631

PCT Pub. Date: Mar. 11, 1999

(30) Foreign Application Priority Data

Sep. 4, 1997 (GB) .............................. 9718737

(51) Int. Cl.[7] ................... C07D 409/02; C07D 239/02; C07D 495/02

(52) U.S. Cl. ........................... 544/315; 549/52; 549/50; 544/229; 544/278; 544/298; 544/315

(58) Field of Search ................... 544/229, 278, 544/298, 315, 319; 549/50, 52

(56) References Cited

U.S. PATENT DOCUMENTS 3,755,582 A  8/1973  Bullock ....................... 424/251

FOREIGN PATENT DOCUMENTS

| DE | 2411274 | * | 9/1975 |
| WO | WO 94/26722 | | 11/1994 |
| WO | WO 97/02262 | | 1/1997 |
| WO | 9702262 | * | 1/1997 |
| WO | WO 97/33890 | | 9/1997 |
| WO | WO 97/48684 | | 12/1997 |

* cited by examiner

Primary Examiner—Mukuid J. Shah
Assistant Examiner—Sudhaker B. Patel
(74) Attorney, Agent, or Firm—William A. Teoli, Jr.; Thomas Hamilton

(57) ABSTRACT

Novel pyrimidin-4-one and pyrimidin-4-thione derivatives of formula (I) wherein A is phenyl, thienyl (including all 3 isomers), thiazolyl or pyridyl; X is oxygen or sulfur; $R_1$ is hydrogen, halogen or trimethylsilyl; $R_2$ is hydrogen, halogen or trimethysilyl; and at least one of $R_1$ and $R_2$ is not hydrogen; $R_3$ is $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, —$(CH_2)_n$—$C_3$–$C_8$cycloalkyl which are unsubstitituted or substituted by halogen, $C_1$–$C_6$alkyl or $C_1$–$C_6$haloalkyl, $C_1$–$C_4$alkoxy-$C_1$–$C_6$alkyl; $C_1$–$C_4$alkoxy-$C_2$–$C_6$alkenyl; $C_1$–$C_4$alkoxy-$C_2$–$C_6$alkenyl; $C_1$–$C_4$alkythio-$C_1$–$C_6$alkyl; $C_1$–$C_4$alkylthio-$C_2$–$C_6$alkenyl; $C_1$–$C_4$alkythio-$C_2$–$C_6$alkynyl; mono-$C_1$–$C_4$alkylamin-$C_1$–$C_6$alkyl; mono-$C_1$–$C_4$alkylamin-$C_1$–$C_6$alkenyl; mono-$C_1$–$C_4$alkylamin-$C_2$–$C_6$alkynyl; —$(CH_2)_n$—$C_1$–$C_4$alkoxy-$C_3$–$C_6$cycloalkyl; —$(CH_2)_n$—$C_1$–$C_4$alkylthio-$C_3$–$C_6$cycloalkyl; —$(CH_2)_2$-mono-$C_1$–$C_4$alkylamin-$C_3$–$C_6$cycloalkyl; or N=$CR_9R_{10}$; n is 1, 2, 3, or 4; $R_4$, $R_5$, $R_6$, $R_7$, and $R_8$ are each independently of the other hydrogen, $C_1$–$C_4$alkyl, $C_1$–$C_4$haloalkyl or halogen, wherein at least one of the substituents $R_4$–$R_8$ must be different from hydrogen; and $R_9$ is hydrogen, $C_1$–$C_6$alkyl, $C_3$–$C_7$cycloalkyl, pyridyl, furyl, thienyl or phenyl which is unsubstituted or mono to pentasubstituted by halogen, $C_1$–$C_6$alkyl, $C_1$–$C_6$haloalkyl, $C_1$–$C_6$alkoxy or $C_1$–$C_6$haloalkoxy; $R_{10}$ is hydrogen, $C_1$–$C_6$alkyl, $C_3$–$C_7$cycloalkyl, pyridyl, furyl, thienyl or phenyl which is unsubstituted or mono to pentasubstituted by halogen, $C_1$–$C_6$alkyl, $C_1$–$C_6$haloalkyl, $C_1$–$C_6$alkoxy or $C_1$–$C_6$haloalkoxy; and at least one of $R_9$ and $R_{10}$ is not hydrogen. The novel compounds have plant-protective properties and are suitable for protecting plants against infestation by phytopathogenic microorganisms, in particular fungi.

12 Claims, No Drawings

PYRIMIDIN-2-OXY-4-ONE AND PYRIMIDIN-2-OXY-4-THIONE DERIVATIVES

The present invention relates to novel pyrimidin-4-one and pyrimidin-4-thione derivatives of formula I, which have pesticidal activity, in particular fungicidal activity,

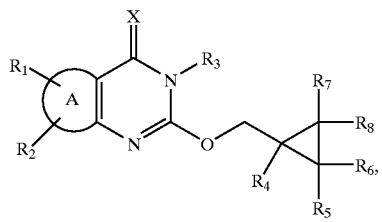

wherein
A is phenyl, thienyl (including all 3 isomers), thiazolyl or pyridyl;
is oxygen or sulfur;
$R_1$ is hydrogen, halogen or trimethylsilyl;
$R_2$ is hydrogen, halogen or trimethylsilyl; at least one of $R_1$ and $R_2$ is not hydrogen;
$R_3$ is $C_1-C_6$alkyl, $C_1-C_6$haloalkyl, $C_2-C_6$alkenyl, $C_2-C_6$haloalkenyl, $C_2-C_6$alkynyl, $C_2-C_6$haloalkynyl, $-(CH_2)_n-C_3-C_8$cycloalkyl which are unsubstituted or mono- to tri-substituted by halogen, $C_1-C_6$alkyl or $C_1-C_6$haloalkyl; $C_1-C_4$alkoxy-$C_1-C_6$alkyl; $C_1-C_4$alkoxy-$C_2-C_6$alkenyl; $C_1-C_4$alkoxy-$C_2-C_6$alkynyl; $C_1-C_1-C_4$alkylthio-$C_1-C_6$alkyl; $C_1-C_4$alkylthio-$C_2-C_6$alkenyl; $C_1-C_4$alkylthio-$C_2-C_6$alkynyl; mono-$C_1-C_4$alkylamin-$C_1-C_6$alkyl; mono-$C_1-C_4$alkylamin-$C_2-C_6$alkenyl; mono-$C_1-C_4$alkylamin-$C_2-C_6$alkynyl; $-(CH_2)_n-$ $C_1-C_4$alkoxy-$C_3-C_6$cycloalkyl; $-(CH_2)_n-$ $C_1-C_4$alkylthio-$C_3-C_6$cycloalkyl; $-(CH_2)_n$-mono-$C_1-C_4$alkylamin-$C_3-C_6$cycloalkyl; or $N=CR_9R_{10}$;
n is 1, 2, 3 or 4;
$R_4$, $R_5$, $R_6$, $R_7$ and $R_8$ are each independently of the other hydrogen, $C_1-C_4$alkyl, $C_1-C_4$haloalkyl or halogen, wherein at least one of the substituents $R_4-R_8$ must be from hydrogen; and
$R_9$ is hydrogen, $C_1-C_6$alkyl, $C_3-C_7$cycloalkyl, pyridyl, furyl, thienyl or phenyl which is unsubstituted or mono to pentasubstituted by halogen, $C_1-C_6$alkyl, $C_1-C_6$haloalkyl, $C_1-C_6$alkoxy or $C_1-C_6$haloalkoxy;
$R_{10}$ is hydrogen, $C_1-C_6$alkyl, $C_3-C_7$cycloalkyl, pyridyl, furyl, thienyl or phenyl which is unsubstituted or mono to pentasubstituted by halogen, $C_1-C_6$alkyl, $C_1-C_6$haloalkyl, $C_1-C_6$alkoxy or $C_1-C_6$haloalkoxy; and at least one of $R_9$ and $R_{10}$ is not hydrogen.

The invention also relates to the preparation of these compounds, to agrochemical compositions comprising as active ingredient at least one of these compounds, as well as to the use of the active ingredients or compositions for pest control, in particular as fungicides, in agriculture and horticulture.

The compounds I and, optionally, their tautomers may be obtained in the form of their salts. Because the compounds I have at least one basic center they can, for example, form acid addition salts. Said acid addition salts are, for example, formed with mineral acids, typically sulfuric acid, a phosphoric acid or a hydrogen halide, with organic carboxylic acids, typically acetic acid, oxalic acid, malonic acid, maleic acid, fumaric acid or phthalic acid, with hydroxycarboxylic acids, typically ascorbic acid, lactic acid, malic acid, tartaric acid or citric acid, or with benzoic acid, or with organic sulfonic acids, typically methanesulfonic acid or p-toluenesulfonic acid.

Together with at least one acidic group, the compounds of formula I can also form salts with bases. Suitable salts with bases are, for example, metal salts, typically alkali metal salts or alkaline earth metal salts, e.g. sodium salts, potassium salts or magnesium salts, or salts with ammonia or an organic amine, e.g. morpholine, piperidine, pyrrolidine, a mono-, di- or trialkylamine, typically ethylamine, diethylamine, triethylamine or dimethylpropylamine, or a mono-, di- or trihydroxyalkylamine, typically mono-, di- or triethanolamine. Where appropriate, the formation of corresponding internal salts is also possible. Within the scope of this invention, agrochemical acceptable salts are preferred.

Where asymmetrical carbon atoms are present in the compounds of formula I, these compounds are in optically active form. Owing to the presence of double bonds, the compounds can be obtained in the [E] and/or [Z] form. Atropisomerism can also occur. The invention relates to the pure isomers, such as enantiomers and diastereomers, as well as to all possible mixtures of isomers, e.g. mixtures of diastereomers, racemates or mixtures of racemates.

The general terms used hereinabove and hereinbelow have the following meanings, unless otherwise defined:

Alkyl groups on their own or as structural element of other groups such as alkoxy are, in accordance with the number of carbon atoms, straight-chain or branched and will typically be methyl, ethyl, n-propyl, isopropyl, n-butyl, sec-butyl, isobutyl, tert-butyl, n-amyl, tert-amyl, 1-hexyl or 3-hexyl.

Alkenyl will be understood as meaning straight-chain or branched alkenyl such as allyl, methallyl, 1-methylvinyl or but-2-en-1-yl. Preferred alkenyl radicals contain 3 to 4 carbon atoms in the chain.

Alkynyl can likewise, in accordance with the number of carbon atoms, be straight-chain or branched and is typically propargyl, but-1-yn-1-yl or but-1-yn-3-yl. The preferred meaning is propargyl.

Halogen and halo substituents will be understood generally as meaning fluorine, chlorine, bromine or iodine. Fluorine, chlorine or bromine are preferred meanings.

Haloalkyl can contain identical or different halogen atoms, typically fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl, 3,3,3-trifluoropropyl.

Cycloalkyl is, depending on the ring size, cyclopropyl, cyclobutyl, cyclopentyl, cyclohexyl, cycloheptyl or cyclooctyl.

Preferred compounds are those of formula I, wherein
A is thienyl, including all 3 isomers and
X is oxygen (subgroup A).

Within the scope of said subgroup A, those compounds of formula I are preferred wherein
$R_1$ is hydrogen, fluorine, chlorine, bromine or iodine;
$R_2$ is hydrogen, fluorine, chlorine, bromine or iodine; at least one of $R_1$ and $R_2$ is not hydrogen;
$R_3$ is $C_1-C_4$alkyl, $C_2-C_4$alkenyl, $C_2-C_4$alkynyl, $C_1-C_4$haloalkyl, $C_2-C_4$haloalkenyl, $C_2-C_4$haloalkynyl or $CH_2-C_3-C_4$cycloalkyl which are unsubstituted or substituted by halogen, $C_1-C_4$alkyl or $C_1-C_4$haloalkyl;
$R_4$, $R_5$, $R_6$, $R_7$ and $R_8$ are each independently of the other hydrogen, fluorine, chlorine, bromine, iodine, $C_1$–$C_4$alkyl or $C_1$–$C_4$haloalkyl, wherein at least one of the substituents $R_4$–$R_8$ must be different from hydrogen (subgroup B).

Within the scope of subgroup B those compounds of formula I are particularly preferred, wherein $R_3$ is $C_1$–$C_4$alkyl, $C_2$–$C_4$alkenyl, $C_2$–$C_4$alkynyl, each of which is unsubstituted or substituted by chlorine or bromine; or $CH_2$—$C_3$–$C_6$cycloalkyl, which is unsubstituted or substituted by fluorine, chlorine, bromine or iodine;

$R_4$, $R_5$, $R_6$, $R_7$ and $R_8$ are each independently of the other hydrogen, fluorine, chlorine, bromine, iodine, $C_1$–$C_4$alkyl or $C_1$–$C_2$haloalkyl, wherein at least one of the substituents $R_4$–$R_8$ must be different from hydrogen (subgroup C).

A special group within the scope of subgroup C is that of the compounds of formula I, wherein $R_1$ is hydrogen, chlorine or bromine;

$R_2$ is hydrogen, chlorine or bromine; at least one of $R_1$ and $R_2$ is not hydrogen;

$R_3$ is $C_1$–$C_4$alkyl or $CH_2$-cyclopropyl;

$R_4$, $R_5$, $R_6$, $R_7$ and $R_8$ are each independently of the other hydrogen, chlorine, bromine, iodine, $C_1$–$C_4$alkyl or $C_1$–$C_2$haloalkyl, wherein at least one of the substituents $R_4$–$R_8$ must be different from hydrogen (subgroup D).

A preferred group within the scope of subgroup D is that of the compounds of the formula I, wherein A is thienyl[2.3-d], $R_3$ is $C_3$–$C_4$alkyl, $R_4$, $R_5$, $R_6$, $R_7$ and $R_8$ are each independently of the other hydrogen, chlorine, bromine, methyl or $CF_3$, wherein at least one of the substituents $R_4$–$R_8$ must be different from hydrogen (subgroup E).

Another preferred group within the scope of subgroup D is that of the compounds of the formula I, wherein A is thienyl[3.2-d];

$R_3$ is $C_3$–$C_4$alkyl;

$R_4$, $R_5$, $R_6$, $R_7$ and $R_8$ are each independently of the other hydrogen, chlorine, bromine, methyl or $CF_3$, wherein at least one of the substituents $R_4$-$R_8$ must be different from hydrogen (subgroup F).

Another preferred compounds are those of formula I, wherein

A is phenyl, and

X is oxygen (subgroup G).

Within the scope of said subgroup G, those compounds of formula I are preferred wherein $R_1$ is hydrogen, fluorine, chlorine, bromine or iodine;

$R_2$ is hydrogen, fluorine, chlorine, bromine or iodine; at least one of $R_1$ and $R_2$ is not hydrogen;

$R_3$ is $C_1$–$C_4$alkyl, $C_2$–$C_4$alkenyl, $C_2$–$C_4$alkynyl, $C_1$–$C_4$haloalkyl, $C_2$–$C_4$haloalkenyl, $C_2$–$C_4$haloalkynyl or $CH_2$—$C_3$–$C_4$cycloalkyl which are unsubstituted or substituted by halogen, $C_1$–$C_4$alkyl or $C_1$–$C_4$haloalkyl;

$R_4$, $R_5$, $R_6$, $R_7$ and $R_8$ are each independently of the other hydrogen, fluorine, chlorine, bromine, iodine, $C_1$–$C_4$alkyl or $C_1$–$C_4$haloalkyl, wherein at least one of the substituents $R_4$–$R_8$ must be different from hydrogen (subgroup H).

Within the scope of subgroup H those compounds of formula I are particularly preferred, wherein $R_3$ is $C_1$–$C_4$alkyl, $C_2$–$C_4$alkenyl or $C_2$–$C_4$alkynyl, each of which is unsubstituted or substituted by chlorine or bromine; $CH_2$—$C_3$–$C_6$cycloalkyl, which is unsubstituted or substituted by fluorine, chlorine, bromine or iodine;

$R_4$, $R_5$, $R_6$, $R_7$ and $R_8$ are each independently of the other hydrogen, fluorine, chlorine, bromine, iodine, $C_1$–$C_4$alkyl or $C_1$–$C_2$haloalkyl, wherein at least one of the substituents $R_4$–$R_8$ must be different from hydrogen (subgroup J).

A special group within the scope of subgroup J is that of the compounds of formula I, wherein $R_1$ is hydrogen, chlorine or bromine;

$R_2$ is hydrogen, chlorine or bromine; at least one of $R_1$ and $R_2$ is not hydrogen;

$R_3$ is $C_1$–$C_4$alkyl or $CH_2$-cyclopropyl;

$R_4$, $R_5$, $R_6$, $R_7$ and $R_8$ are each independently of the other hydrogen, chlorine, bromine, iodine or $C_1$–$C_4$alkyl, wherein at least one of the substituents $R_4$–$R_8$ must be different from hydrogen (subgroup K).

Another preferred compounds are those of formula I, wherein

A is pyridyl, and

X is oxygen (subgroup L).

Within the scope of said subgroup L, those compounds of formula I are preferred wherein $R_1$ is hydrogen, fluorine, chlorine, bromine or iodine;

$R_2$ is hydrogen, fluorine, chlorine, bromine or iodine; at least one of $R_1$ and $R_2$ is not hydrogen;

$R_3$ is $C_1$–$C_4$alkyl, $C_2$–$C_4$alkenyl, $C_2$–$C_4$alkynyl, $C_1$–$C_4$haloalkyl, $C_2$–$C_4$haloalkenyl, $C_2$–$C_4$haloalkynyl or $CH_2$—$C_3$–$C_4$cycloalkyl which are unsubstituted or substituted by halogen, $C_1$–$C_4$alkyl or $C_1$–$C_4$haloalkyl;

$R_4$, $R_5$, $R_6$, $R_7$ and $R_8$ are each independently of the other hydrogen, fluorine, chlorine, bromine, iodine, $C_1$–$C_4$alkyl or $C_1$–$C_4$haloalkyl, wherein at least one of the substituents $R_4$–$R_8$ must be different from hydrogen (subgroup M).

Within the scope of subgroup M those compounds of formula I are particularly preferred, wherein $R_3$ is $C_1$–$C_4$alkyl, $C_2$–$C_4$alkenyl or $C_2$–$C_4$alkynyl, each of which is unsubstituted or substituted by chlorine or bromine; or $CH_2$—$C_3$–$C_6$cycloalkyl, which is unsubstituted or substituted by fluorine, chlorine, bromine or iodine;

$R_4$, $R_5$, $R_6$, $R_7$ and $R_8$ are each independently of the other hydrogen, fluorine, chlorine, bromine, iodine, $C_1$–$C_4$alkyl or $C_1$–$C_2$haloalkyl, wherein at least one of the substituents $R_4$–$R_8$ must be different from hydrogen (subgroup N).

A special group within the scope of subgroup N is that of the compounds of formula I, wherein $R_1$ is hydrogen, chlorine or bromine;

$R_2$ is hydrogen, chlorine or bromine; at least one of $R_1$ and $R_2$ is not hydrogen;

$R_3$ is $C_1$–$C_4$alkyl or $CH_2$-cyclopropyl;

$R_4$, $R_5$, $R_6$, $R_7$ and $R_8$ are each independently of the other hydrogen, chlorine, bromine, iodine or $C_1$–$C_4$alkyl, wherein at least one of the substituents $R_4$–$R_8$ must be different from hydrogen (subgroup P).

The most preferred compounds of the invention disclosed herein are the following ones:

6-bromo-2-(1-methylcyclopropylmethoxy)-3-n-propyl-3Hquinazoline-4-one (no. 1.7), 6-bromo-2-(2-methylcyclopropylmethoxy)-3-n-propyl-3H-quinazoline-4-one (no. 1.22), 6-bromo-2-(1-methylcyclopropylmethoxy)-3-n-buyl-3H-quinazoline-4-one (no. 1.10), 6-bromo-2-(2-methylcyclopropylmethoxy)-3-n-buyl-3H-quinazoline-4-one (no. 1.25), 6-bromo-2-(1-methylcyclopropylmethoxy)-3-n-propyl-3H-thieno[2.3-d]pyrimidin-4-one (no. 3.7), 6-chloro-2-(1-methylcyclopropylmethoxy)-3-n-propyl-3H-thieno[2.3-d]pyrimidin-4-one (no. 3.6), 6-bromo-2-(2-methylcyclopropylmethoxy)-3-n-propyl-3H-thieno[2.3-d]pyrimidin-4-one (no. 3.22), 6-chloro-2-(2-methylcyclopropylmethoxy)-3-n-propyl-3H-thieno[2.3-d]pyrimidin-4-one (no. 3.21), 6-bromo-2-(1-methylcyclopropylmethoxy)-3-n-buyl-3H-thieno[2.3-d]pyrimidin-4-one (no. 3.10), 6-chloro-2-(1-methylcyclopropylmethoxy)-3-n-buyl-3H-thieno[2.3-d]pyrimidin-4-one (no. 3.9), 6-bromo-2-(2-methylcyclopropylmethoxy)-3-n-buyl-3H-thieno[2.3-d]pyrimidin-4-one (no. 3.25), 6-chloro-2-(2-methylcyclopropylmethoxy)-3-n-buyl-3H-thieno[2.3-d]pyrimidin-4-one (no. 3.24).

The compounds of formula I can be prepared as follows:

Scheme 1 prepared, for example, in accordance with Acta Pharm. Suecica 1968, Vol. 5, p.563, according to S. Gronowitz et al. Other heterocycles can be prepared according to instructions in the literature. The synthesis of, for example, ethyl 5-aminothiazole-4-carboxylate and ethyl 5-amino-2-methylthiazole-4-carboxylate is described by Golankiewicz et al. in Tetrahedron 1985, 41, 5989. The reaction of the α-amino-β-carboalkoxyheterocycles or α-amino->carbocyclic acid heterocycles with thiophosgene (step 1 a in scheme 1) is conveniently carried out in the presence of a base, such as NaOH, KOH, $CaCO_3$, $Na_2CO_3$, $K_2CO_3$, $NaHCO_3$, $N(Et)_3$, pyrimidin, and others, in solvents, such as $CH_2Cl_2$, $CHCl_3$, ether, tetrahydrofuran and others, possibly in a 2 phase mixture consisting of $CHCl_3$/water or $CH_2Cl_2$/water, or toluene/water in the temperature range from 0° C. to reflux temperature. The resulting isothiocyanates are then converted with primary amines, such as n-butylamine, n-propylamine, isopropylamine, allylamine, propargylamine, cyclopropylamine, and others, in a solvent (ether, tetrahydrofuran, $CH_2Cl_2$, $CHCl_3$, benzene, toluene, dimethylformamide, dimethylsulfoxide) at 0° C. to reflux

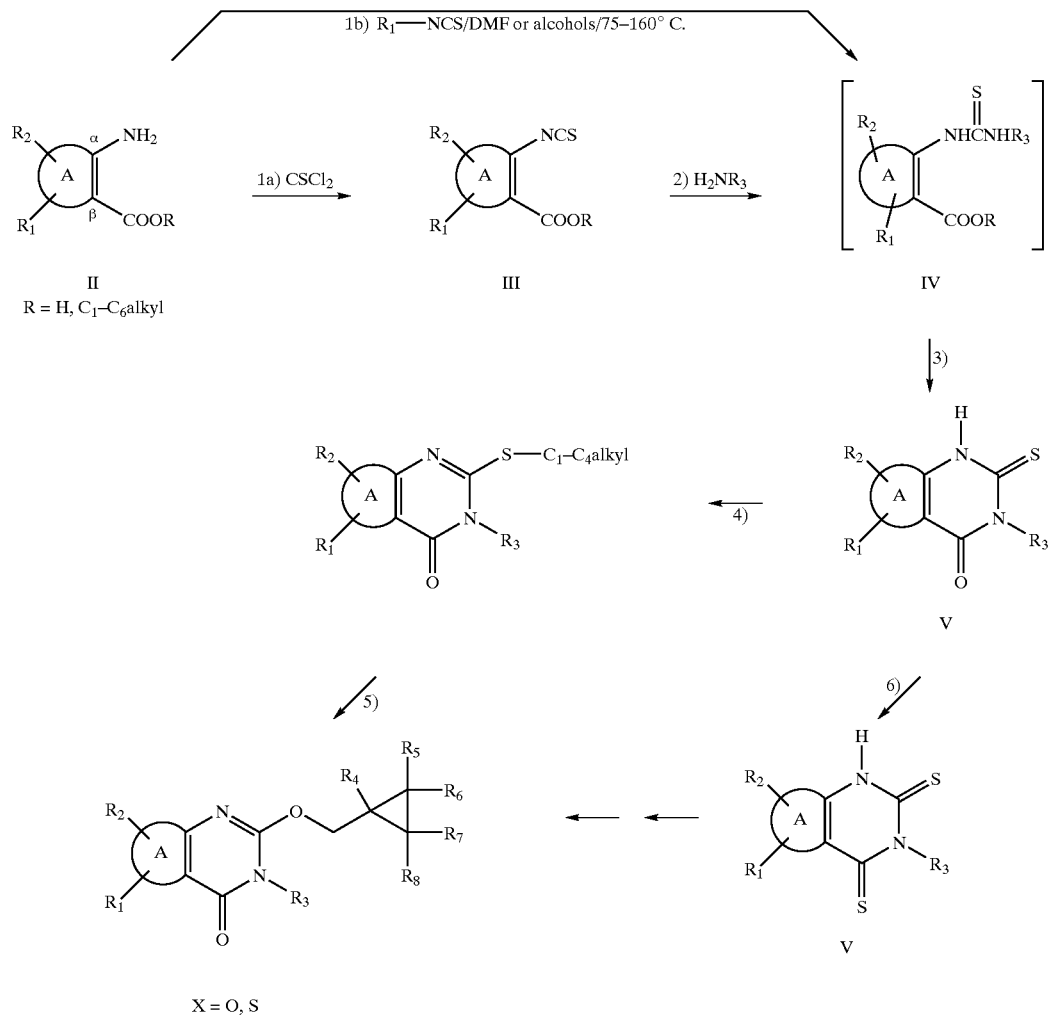

The compounds of formula I are preferably prepared starting from α-amino-β-carboalkoxyheterocycles or (α-amino-β-carbocyclic acid heterocycles, some of which, where Het=thienyl, are commercially available (2 isomers). The methyl thiophene-2-amino-3-carboxylate can be temperature into the thioureaheterocycles IV (step 2 in scheme 1), which can also be prepared via reaction of the heterocyclic amines II with isothiocyanatoalkanes such as 1-isothiocyanatopropane, 1-isothiocyanatobutane and others in ethanol, n-propanol, n-butanol, dimethylformamide, dimethylacetamide or dimethylsulfoxide as solvents at temperatures between 50° C. and reflux temperature (step 1b in scheme 1). The thioureaheterocycles IV, in most cases, cyclise immediately (step 3 in scheme 1). In some cases, the cyclysation is carried out in the presence of stronger bases, such as potassium tert-butylate, sodium hydride or potassium hydride in solvents such as tetrahydrofuran, dimethylfomamide or dimethylsulfoxide in the temperature range from 20°–140° C. The 2-thioxopyrimidin-4-one derivatives are then deprotonised (using bases such as NaOH, NaH, KH, n-BuLi, $Na_2CO_3$, $K_2CO_3$ etc.) and are then S-alkylated by the addition of alkylhalides (halo=Br, I) (step 4 in scheme 1). The reaction with methyliodide results in the 2-methylsulfanylpyrimidin-4-one derivative which is an important intermediate for the synthesis of alkoxy-substituted and aminoalkyl-substituted pyrimidin-4-ones. The replacement of the thiomethyl group (step 5 in scheme 1) with alkoxy is most preferably carried out by reaction with metal alkoxides, such as $NaOCH_2$-(2-methyl-cyclopropyl), $NaOCH_2$-(1-methyl-cyclopropyl), $NaOCH_2$-(2,2-dichlor-cyclopropyl), $NaOCH_2$-(2,2-difluorcyclopropyl), etc., in the corresponding alcohol, tetrahydrofurane, dioxane or dimethylsulfoxide as solvent in the temperature range from 20°–150° C.

The replacement of the 4-one group with sulfur to the 4-thione group (step 6 in scheme 1) is carried out by reaction with $P_2S_5$ or Lawesson-reagent in tetrahydrofurane, dioxane or toluene as solvent in the temperature range from 20° C.—reflux temperature.

The above synthesis route is the first disclosure of how to prepare 3H-thieno[2.3-d]-pyrimidin-4-one derivatives within the structural pattern of formula I herein.

The invention also relates to the intermediates of the formula IV and V, and especially to those wherein A represents thienyl[2.3-d].

The introduction of further substituents into the 5-ring of the thienopyrimidin-4-ones may also conveniently be carried out using metallorganic methodology. Thieno[3.2-d]-pyrimidin-4-ones and thieno[2.3-d]pyrimidin-4-ones, for example, can be deprotonised selectively in 6-position. Particularly suitable bases for this purpose are lithium diisopropylamide (LDA), lithium cyclohexylisopropylamide (LICA) or secondary butyl lithium/TMEDA. A great number of the radicals $R_1$ or $R_2$ indicated above can be introduced by reacting the resulting anions with electrophiles (step 1 in scheme 2), typically $Br_2$, NBS, $F_2$, ICl, $Cl_2$, $F^+$ reagents, trimethylsilyl chloride.

Scheme 2

Synthesis of Special Heterocycles

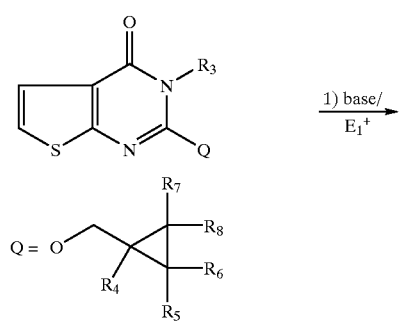

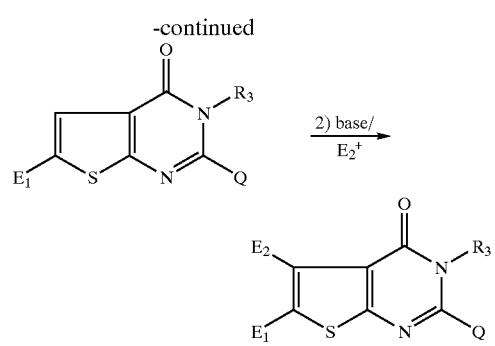

$E^+_{1.2}$=NBS (N-Bromsuccinimide), NCS (N-Chlorsuccinimide), $Cl_2$, Br, FCl, F reagents, TMS and similar Si reagents.

The following compounds can likewise be prepared in general accordance with the methods described in scheme 2:

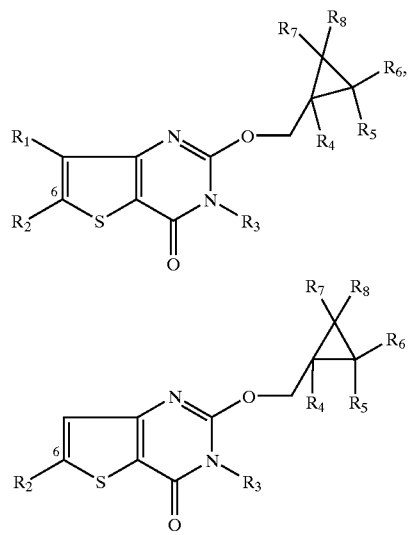

Scheme 3

Synthesis of Special Thienopyrimidin-4-ones
(Special Methods for the Introduction of Halogen into the Thiophene Ring)

a) Thieno[2.3-d]pyrimidin-4-ones:

a1)

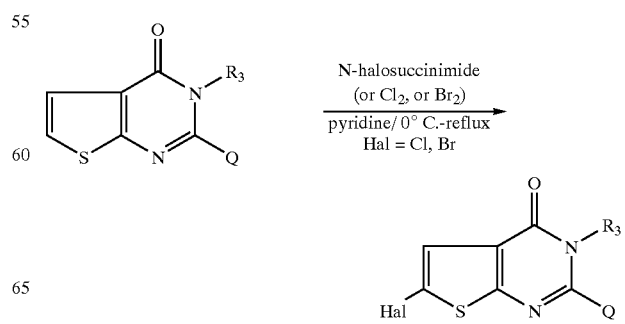

-continued

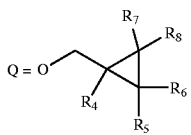

1–3 molar equivalents of N-bromosuccinimide or N-chlorosuccinimide (or Cl$_2$ gas or Br$_2$) are used for halogenation. The solvent used is, for example, pyrimidin in the temperature range from 0° C. to reflux. The reaction time is 1 to 24 hours.

a2) "Pure" Chlorinating Method

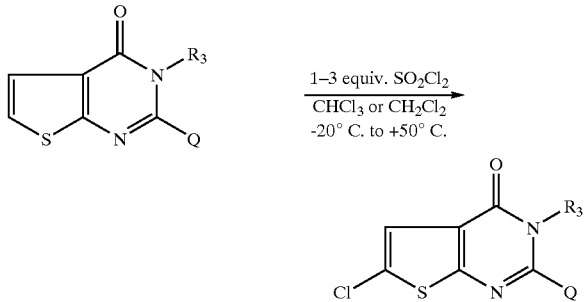

The described reactions are carried out in per se known manner, e.g. in the presence or absence of a suitable solvent or diluent or of a mixture thereof, if appropriate with cooling, at room temperature or with heating, e.g. in the temperature range from about −20° C. to the boiling temperature of the reaction medium, preferably in the range from about −20° C. to about +150° C. and, if required, in a closed vessel, under pressure, in an inert gas atmosphere and/or under anhydrous conditions.

Illustrative examples of such solvents or diluents are: aromatic, aliphatic and alicyclic hydrocarbons and halogenated hydrocarbons, typically benzene, toluene, xylene, chlorobenzene, bromobenzene, petroleum ether, hexane, cyclohexane, dichloromethane, trichloromethane, dichloroethane or trichloroethane; ethers, typically diethyl ether, tert-butylmethyl ether, tetrahydrofuran or dioxane; ketones, typically acetone or methyl ethylketone; alcohols, typically methanol, ethanol, propanol, butanol, ethylene glycol or glycerol; esters, typically ethyl acetate or butyl acetate; amides, typically N,N-dimethylformamide, N,N-dimethylacetamide, N-methylpyrrolidone or hexamethylphosphoric acid triamide; nitriles, typically acetonitrile; and sulfoxides, typically dimethylsulfoxide. Bases used in excess, such as triethylamine, pyrimidin, N-methylmorpholine or N,N-diethylaniline, can also be used as solvents or diluents.

Suitable bases are, for example, alkali metal hydroxide or alkaline earth metal hydroxide, alkali metal hydride or alkaline earth metal hydride, alkali metal amide or alkaline earth metal amide, alkali metal alkanolate or alkaline earth metal alkanolate, alkali metal carbonate or alkaline earth metal carbonate, alkali metal dialkylamide or alkaline earth metal dialkylamide, or alkali metal alkylsilylamide or alkaline earth metal alkylsilylamide, alkylamines, alkylenediamines, optionally N-alkylated, optionally unsaturated cycloalkylamines, basic heterocycles, ammonium hydroxides and carbocyclic amines. Examples meriting mention are sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyltrimethylammonium hydroxide, and 1,8-diazabicyclo[5.4.0]undec-5-ene (DBU).

Quinazolinone derivatives having fungicidal properties are known from WO-94/26722 or EP-A-276825 and thienopyrimidinones are known from WO-97/02262.

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. Botrytis, Pyricularia, Helminthosporium, Fusarium, Septoria, Cercospora and Altemaria) and Basidiomycetes (e.g. Rhizoctonia, Hemileia, Puccinia). Additionally, they are also effective against the Ascomycetes classes (e.g. Venturia and Erysiphe, Podosphaera, Monilinia, Uncinula) and of the Oomycetes classes (e.g. Phytophthora, Pythium, Plasmopara). Furthermore, the novel compounds of formula I are effective against phytopathogenic bacteria and viruses (e.g. against Xanthomonas spp, Pseudomonas spp, Erwinia amylovora as well as against the tobacco mosaic virus).

Within the scope of this invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula I are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129 or 2-[α{[(α-methyl-3-trifluoromethyl-benzyl)imino]-oxy}-o-tolyl]-glyoxylic acid-methylester-O-methyloxime; dithiocarbamates such as ferbam, mancozeb, maneb, metiram, propineb, thiram, zineb or ziram; N-halomethylthiodicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chiorothalonil, cymoxanil, dichlone, diclomezine, dicloran, diethofencarb, dimethomorph, dithianon, etridiazole, famoxadone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine or validamycin.

Suitable carriers and adjuvants can be solid or liquid and are substances useful in formulation technology, e.g. natural or regenerated mineral substances, solvents, dispersants, wetting agents, tackifiers, thickeners, binders or fertilizers.

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g active substance per kg of seeds.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers. Such carriers are for example described in WO 97/33890.

Further surfactants customarily employed in the art of formulation are known to the expert or can be found in the relevant literature.

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25 from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

The following non-limitative Examples illustrate the above-described invention in more detail. Temperatures are given in degrees Celsius. The following abbreviations are used: Et=ethyl; i-propyl=isopropyl; Me=methyl; m.p.=melting point. "NMR" means nuclear magnetic resonance spectrum. MS=mass spectrum. "%" is percent by weight, unless corresponding concentrations are indicated in other units.

PREPARATION EXAMPLES

Example P-1

Methyl 2-Isothiocyanatothiophene-3-Carboxylate

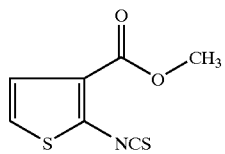

In a sulfonation flask, 50.2 g (0.32 mol) of methyl 2-aminothiophene-3-carboxylate are added to 480 ml of chloroform and 320 ml of water. Then 40.5 g (0.35 mol and 1000 ml of saturated aqueous sodium bicarbonate solution are added simultaneously in 40 minutes under stirring. The stirring continued for 1 h at room temperature and then the organic phase is separated. The water phase is extracted twice with chloroform and the organic phase dried over sodium sulfate. After removal of the chloroform in the water-jet vacuum 61.3 g of a dark oil is obtained, which is further purified by column chromatography over silica gel (eluant: ethyl acetate/hexane=1:5). 41.5 g of methyl 2-isothiocyanato-thiophene-3-carboxylate are obtained in the form of a brown powder having a melting point of 63–65° C.

Example P-2 (Method 1)

Methyl 2-(3-propylthioureido)thiophene-3-carboxylate

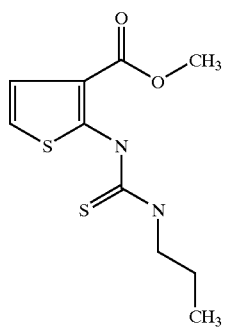

In a sulfonation flask, 13.5 g (0.023 mol) of n-propylamine are added dropwise to 350 ml of tetrahydrofurane and 41.3 g (0.021 mol) of methyl 2-isothiocyanatothiophene-3-carboxylate, such that the internal temperature does not arise above 40° C. The reaction mixture is then stirred for 4 hours at reflux temperature and then the tetrahydrofurane is removed in a water-jet vacuum. The residue is taken up in ethyl acetate and extracted three times with water. The organic phase is then dried over sodium sulfate and the solvent is removed in the water-jet vacuum, giving the crude product, which is purified by column chromatography over silica gel (eluant: ethyl acetate/hexane=1:3). 32.4 g of methyl 2-(3-propylthioureido)thiophene-3-carboxylate are obtained in the form of a beige powder having a melting point of 123–126° C.

Example P-2 (Method 2)

Methyl 2-(3-Propylthioureido)thiophene-3-Carboxylate

In a sulfonation flask, 2.02 g (0.02 mol) of 1-isothiocynatopropane are added dropwise to 30 ml dimethylformamide and 3.0 g (0.019 mol) of methyl 2-aminothiophene-3-carboxylate. The reaction mixture is then stirred at 130–135° C. for 12 hours and after cooling added to 120 ml of water. The resulting mixture is then extracted three times with ethylacetate and the separated organic phase dried over sodium sulfate. The solvent is then removed in a water-jet vacuum, giving the crude product as a dark oil, which is purified by column chromatography over silica gel (eluant: tert.butylmethylether/hexane=2:3). 2.0 g of methyl 2-(3-propylthioureido)thiophene-3-carboxylate are obtained in the form of a yellow powder having a melting point of 122–124° C.

Example P-3

3-Butyl-2-thioxo-2,3-dihydro-1H-thieno[2.3-d]pyrimidin-4-one

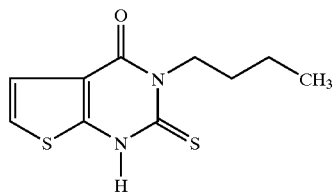

In a sulfonation flask, 0.2 g (0.0049 mol) of a ca. 60% sodium hydride dispersion is added to 20 ml absolute tetrahydrofurane. Then 1.29 g (0.0047 mol) of methyl 2-(3-butylthioureido)thiophene-3-carboxylate, dissolved in 10 ml absolute tetrahydrofurane are added dropwise, such that the internal temperature remains constant at about 25° C. The mixture is stirred at reflux temperature for 3 hours and then the solvent is removed in a water-jet vacuum and the residue taken up in ethylacetate/water. After addition of acetic acid the mixture is extracted three times with ethylacetate and the organic phase dried over sodium sulfate. After removal of the solvent in a water-jet vacuum, 1.06 g of 3-butyl-2-thioxo-2,3-dihydro-1H-thieno[2.3-d]pyrimidin-4-one are obtained in the form of a brown powder having a melting point of 200–203° C.

Example P-4

2-Methylsulfanyl-3-propyl-3H-thieno[2.3-d]pyrimidin-4-one

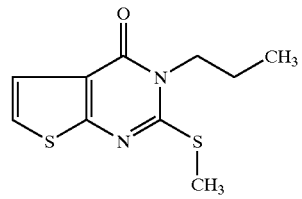

In a sulfonation flask, 2.9 g (0.072 mol) of a ca. 60% sodium hydride dispersion is added to 50 ml of absolute tetrahydrofurane. Then 17.7 g (0.069 mol) of methyl 2-(3-propylthioureido)thiophene-3-carboxylate, dissolved in 100 ml of absolute tetrahydrofurane, are added dropwise, such that the internal temperature remains constant at about 25° C. The mixture is stirred at reflux temperature for 5 hours and after cooling to room temperature 10.9 g (0.077 mol) of methyliodide, dissolvedin 10 ml of tetrahydrofurane, are added dropwise. Then the mixture is stirred another 2 hours at reflux temperature. After completion of the reaction, the tetrahydrofurane is removed in the waterjet vacuum and the residue taken up in ethyl acetate. The organic layer is washed twice with water and then dried over sodium sulfate. After removal of the solvent in the water-jet vacuum, the crude product is obtained, which is purified by digestion in n-hexane. 15.1 g of 2-methylsulfanyl-3-propyl-3H-thieno[2.3-d]pyrimidin-4-one are obtained in the form of a slightly yellowish powder having a melting point of 94–96° C.

Example P-5

2-(2,2-Dichlorocyclopropylmethoxy)-3-n-propyl-3H-thieno[2.3-d]pyrimidin-4-one

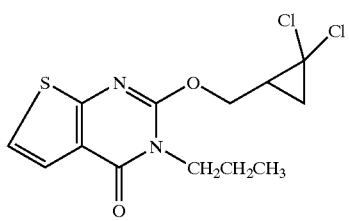

In a sulfonation flask, 2.8 g (0.02 mol) of 2,2-dichlorocyclopropanmethanol are added to 40 ml of absolute tetrahydrofurane and under stirring 0.6 g (0.015 mol) NaH-dispersion is carefully added. After stirring for 1 hour at room temperature, a solution of 2.4 g (0.01 mol) 2-methylsulfanyl-3-propyl-3H-thieno[2.3-d]pyrimidin-4-one in 20 ml tetrahydrofurane was added within 2 minutes. After stirring for 4 hours at room temperature the solvent is removed in a water-jet vacuum and the residue is taken up in TBME and the mixture washed repeatedly with water. The TBME-phase is concentrated in the water-jet vacuum and subsequently the excess 2,2-dichlorocyclopropylmethanol destined in high vacuum. 3.0 g of 2-(2,2-dichlorocyclopropylmethoxy)-3-propyl-3H-thieno[2.3-d]pyrimidin-4-one are obtained in the form of a white powder having a melting point of 64–66° C.

Example P-6

6-chloro-2-(2,2-Dichlorocyclopropylmethoxy)-3-n-propyl-3H-thieno-[2.3-d]pyrimidin-4-one

[cmpd.no. 3.36]

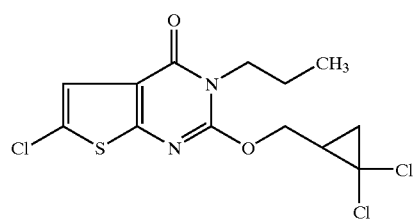

In a sulfonation flask, 1.3 g (0.0039 mol) of 2-(2,2-dichlorocyclopropylmethoxy)-3-propyl-3H-thieno[2.3d]pyrimidin-4-one are added, with stirring, to 15 ml of absolute pyridine. The internal temperature is then raised to 70° C. and then 0.78 g (0.0059 mol) of N-chlorosuccinimide (NCS) are added over about 5 min in smallish portions. After stirring for 2 hours at 70–75° C., the pyridine is removed in a water-jet vacuum. The crude product so obtained is purified by column chromatography over silica gel (eluant: n-hexane/ethyl acetate=4:1), giving 0.55 g of 6-chloro-2-(2, 2-dichlorocyclopropylmethoxy)-3-propyl-3H-thieno[2.3-d]pyrimidin-4-one in the form of a beige powder having a melting point of 94–96° C.

TABLE 1

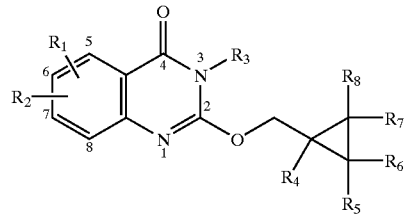

| cmpd. No. | $R_1$ | $R_2$ | $R_3$ | $R_4$ | $R_5$ | $R_6$ | $R_7$ | $R_8$ | phys. data m.p. °C. |
|---|---|---|---|---|---|---|---|---|---|
| 1.1 | 6-Cl | H | Me | Me | H | H | H | H | |
| 1.2 | 6-Br | H | Me | Me | H | H | H | H | |
| 1.3 | H | 7-Cl | Me | Me | H | H | H | H | |
| 1.4 | 6-Cl | H | Et | Me | H | H | H | H | |
| 1.5 | 6-Br | H | Et | Me | H | H | H | H | |
| 1.6 | 6-Cl | H | n-propyl | Me | H | H | H | H | |
| 1.7 | 6-Br | H | n-propyl | Me | H | H | H | H | 81–85 |
| 1.8 | H | 7-Br | n-propyl | Me | H | H | H | H | |
| 1.9 | 6-Cl | H | n-butyl | Me | H | H | H | H | |
| 1.10 | 6-Br | H | n-butyl | Me | H | H | H | H | 66–69 |
| 1.11 | H | 7-Cl | n-butyl | Me | H | H | H | H | |
| 1.12 | 6-Cl | H | i-butyl | Me | H | H | H | H | |
| 1.13 | 6-Br | H | i-butyl | Me | H | H | H | H | |
| 1.14 | 6-Cl | H | cyclo-propyl-CH$_2$ | Me | H | H | H | H | |
| 1.15 | 6-Br | H | cyclo-propyl-CH$_2$ | Me | H | H | H | H | 77–80 |
| 1.16 | 6-Cl | H | Me | H | Me | H | H | H | |
| 1.17 | 6-Br | H | Me | H | Me | H | H | H | |
| 1.18 | H | 7-Cl | Me | H | Me | H | H | H | |
| 1.19 | 6-Cl | H | Et | H | Me | H | H | H | |
| 1.20 | 6-Br | H | Et | H | Me | H | H | H | |
| 1.21 | 6-Cl | H | n-propyl | H | Me | H | H | H | |
| 1.22 | 6-Br | H | n-propyl | H | Me | H | H | H | 49–51 |
| 1.23 | 7-Br | H | n-propyl | H | Me | H | H | H | |
| 1.24 | 6-Cl | H | n-butyl | H | Me | H | H | H | |
| 1.25 | 6-Br | H | n-butyl | H | Me | H | H | H | 68–72 |
| 1.26 | H | 7-Cl | n-butyl | H | Me | H | H | H | |
| 1.27 | 6-Cl | H | i-butyl | H | Me | H | H | H | |
| 1.28 | 6-Br | H | i-butyl | H | Me | H | H | H | |
| 1.29 | 6-Cl | H | cyclo-propyl-CH$_2$ | H | Me | H | H | H | |
| 1.30 | 6-Br | H | cyclo-propyl-CH$_2$ | H | Me | H | H | H | 78–81 |
| 1.31 | 6-Cl | H | Me | H | Cl | Cl | H | H | |
| 1.32 | 6-Br | H | Me | H | Cl | Cl | H | H | |
| 1.33 | H | 7-Cl | Me | H | Cl | Cl | H | H | |
| 1.34 | 6-Cl | H | Et | H | Cl | Cl | H | H | |
| 1.35 | 6-Br | H | Et | H | Cl | Cl | H | H | |
| 1.36 | 6-Cl | H | n-propyl | H | Cl | Cl | H | H | |
| 1.37 | 6-Br | H | n-propyl | H | Cl | Cl | H | H | oil, $^1$H-NMR |
| 1.38 | 7-Br | H | n-propyl | H | Cl | Cl | H | H | |
| 1.39 | 6-Cl | H | n-butyl | H | Cl | Cl | H | H | |
| 1.40 | 6-Br | H | n-butyl | H | Cl | Cl | H | H | |
| 1.41 | H | 7-Cl | n-butyl | H | Cl | Cl | H | H | |
| 1.42 | 6-Cl | H | i-butyl | H | Cl | Cl | H | H | |
| 1.43 | 6-Br | H | i-butyl | H | Cl | Cl | H | H | |
| 1.44 | 6-Cl | H | cyclo-propyl-CH$_2$ | H | Cl | Cl | H | H | |
| 1.45 | 6-Br | H | cyclo-propyl-CH$_2$ | H | Cl | Cl | H | H | |
| 1.46 | 6-Cl | H | Me | H | F | F | H | H | |
| 1.47 | 6-Br | H | Me | H | F | F | H | H | |
| 1.48 | H | 7-Cl | Me | H | F | F | H | H | |
| 1.49 | 6-Cl | H | Et | H | F | F | H | H | |
| 1.50 | 6-Br | H | Et | H | F | F | H | H | |
| 1.51 | 6-Cl | H | n-propyl | H | F | F | H | H | |
| 1.52 | 6-Br | H | n-propyl | H | F | F | H | H | |

TABLE 1-continued

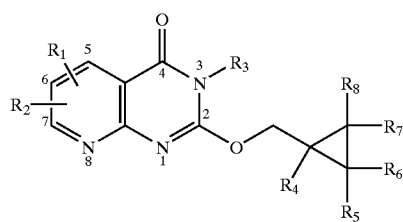

| cmpd. No. | R₁ | R₂ | R₃ | R₄ | R₅ | R₆ | R₇ | R₈ | phys. data m.p. °C. |
|---|---|---|---|---|---|---|---|---|---|
| 1.53 | 7-Br | H | n-propyl | H | F | F | H | H | |
| 1.54 | 6-Cl | H | n-butyl | H | F | F | H | H | |
| 1.55 | 6-Br | H | n-butyl | H | F | F | H | H | |
| 1.56 | H | 7-Cl | n-butyl | H | F | F | H | H | |
| 1.57 | 6-Cl | H | i-butyl | H | F | F | H | H | |
| 1.58 | 6-Br | H | i-butyl | H | F | F | H | H | |
| 1.59 | 6-Cl | H | cyclo-propyl-CH₂ | H | F | F | H | H | |
| 1.60 | 6-Br | H | cyclo-propyl-CH₂ | H | F | F | H | H | |
| 1.61 | 6-Cl | H | n-propyl | H | Me | Me | H | H | |
| 1.62 | 6-Br | H | n-propyl | H | Me | Me | H | H | |
| 1.63 | 6-Cl | H | n-butyl | H | Me | Me | H | H | |
| 1.64 | 6-Br | H | n-butyl | H | Me | Me | H | H | |
| 1.65 | 6-Cl | H | n-propyl | H | Me | H | Me | H | |
| 1.66 | 6-Br | H | n-propyl | H | Me | H | Me | H | |
| 1.67 | 6-Cl | H | n-butyl | H | Me | H | Me | H | |
| 1.68 | 6-Br | H | n-butyl | H | Me | H | Me | H | |

TABLE 2

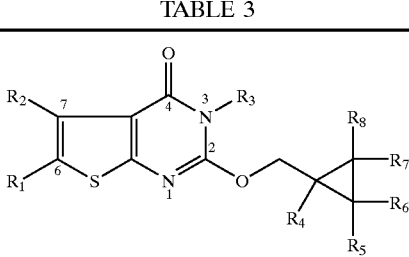

| cmpd. No. | R₁ | R₂ | R₃ | R₄ | R₅ | R₆ | R₇ | R₈ | phys. data m.p. °C. |
|---|---|---|---|---|---|---|---|---|---|
| 2.1 | 6-Cl | H | Me | Me | H | H | H | H | |
| 2.2 | 6-Br | H | Me | Me | H | H | H | H | |
| 2.3 | 6-Br | H | Et | Me | H | H | H | H | |
| 2.4 | 6-Br | H | n-propyl | Me | H | H | H | H | |
| 2.5 | 6-Cl | H | n-butyl | Me | H | H | H | H | |
| 2.6 | 6-Br | H | n-butyl | Me | H | H | H | H | |
| 2.7 | 6-Cl | H | i-butyl | Me | H | H | H | H | |
| 2.8 | 6-Br | H | i-butyl | Me | H | H | H | H | |
| 2.9 | 6-Cl | H | cyclo-propyl-CH₂ | Me | H | H | H | H | |
| 2.10 | 6-Br | H | cyclo-propyl-CH₂ | Me | H | H | H | H | |
| 2.11 | 6-Cl | H | Me | H | Me | H | H | H | |
| 2.12 | 6-Br | H | Me | H | Me | H | H | H | |
| 2.13 | 6-Br | H | Et | H | Me | H | H | H | |
| 2.14 | 6-Br | H | n-propyl | H | Me | H | H | H | |
| 2.15 | 6-Cl | H | n-butyl | H | Me | H | H | H | |
| 2.16 | 6-Br | H | n-butyl | H | Me | H | H | H | |
| 2.17 | 6-Cl | H | i-butyl | H | Me | H | H | H | |
| 2.18 | 6-Br | H | i-butyl | H | Me | H | H | H | |
| 2.19 | 6-Cl | H | cyclo-propyl-CH₂ | H | Me | H | H | H | |
| 2.20 | 6-Br | H | cyclo-propyl-CH₂ | H | Me | H | H | H | |

TABLE 2-continued

| cmpd. No. | R₁ | R₂ | R₃ | R₄ | R₅ | R₆ | R₇ | R₈ | phys. data m.p. °C. |
|---|---|---|---|---|---|---|---|---|---|
| 2.21 | 6-Cl | H | Me | H | Cl | Cl | H | H | |
| 2.22 | 6-Br | H | Me | H | Cl | Cl | H | H | |
| 2.23 | 6-Br | H | Et | H | Cl | Cl | H | H | |
| 2.24 | 6-Br | H | n-propyl | H | Cl | Cl | H | H | |
| 2.25 | 6-Cl | H | n-butyl | H | Cl | Cl | H | H | |
| 2.26 | 6-Br | H | n-butyl | H | Cl | Cl | H | H | |
| 2.27 | 6-Cl | H | i-butyl | H | Cl | Cl | H | H | |
| 2.28 | 6-Br | H | i-butyl | H | Cl | Cl | H | H | |
| 2.29 | 6-Cl | H | cyclo-propyl-CH₂ | H | Cl | Cl | H | H | |
| 2.30 | 6-Br | H | cyclo-propyl-CH₂ | H | Cl | Cl | H | H | |
| 2.31 | 6-Cl | H | Me | H | F | F | H | H | |
| 2.32 | 6-Br | H | Me | H | F | F | H | H | |
| 2.33 | 6-Br | H | Et | H | F | F | H | H | |
| 2.34 | 6-Br | H | n-propyl | H | F | F | H | H | |
| 2.35 | 6-Cl | H | n-butyl | H | F | F | H | H | |
| 2.36 | 6-Br | H | n-butyl | H | F | F | H | H | |
| 2.37 | 6-Cl | H | i-butyl | H | F | F | H | H | |
| 2.38 | 6-Br | H | i-butyl | H | F | F | H | H | |
| 2.39 | 6-Cl | H | cyclo-propyl-CH₂ | H | F | F | H | H | |
| 2.40 | 6-Br | H | cyclo-propyl-CH₂ | H | F | F | H | H | |
| 2.41 | 6-Cl | H | Me | H | Me | Me | H | H | |
| 2.42 | 6-Br | H | Me | H | Me | Me | H | H | |
| 2.43 | 6-Br | H | Et | H | Me | Me | H | H | |
| 2.44 | 6-Br | H | n-propyl | H | Me | Me | H | H | |
| 2.45 | 6-Br | H | n-butyl | H | Me | Me | H | H | |
| 2.46 | 6-Br | H | Et | H | Me | H | Me | H | |
| 2.47 | 6-Br | H | n-propyl | H | Me | H | Me | H | |
| 2.48 | 6-Br | H | n-butyl | H | Me | H | Me | H | |
| 2.49 | 6-Br | H | n-propyl | H | CF₃ | H | H | H | |
| 2.50 | 6-Br | H | n-butyl | H | CF₃ | H | H | H | |

TABLE 3

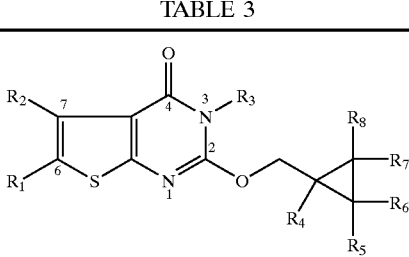

| cmpd. No. | R₁ | R₂ | R₃ | R₄ | R₅ | R₆ | R₇ | R₈ | phys. data m.p. °C. |
|---|---|---|---|---|---|---|---|---|---|
| 3.1 | 6-Cl | H | Me | Me | H | H | H | H | |
| 3.2 | 6-Br | H | Me | Me | H | H | H | H | |
| 3.3 | 6-I | H | Me | Me | H | H | H | H | |
| 3.4 | 6-Cl | H | Et | Me | H | H | H | H | |
| 3.5 | 6-Br | H | Et | Me | H | H | H | H | |
| 3.6 | 6-Cl | H | n-propyl | Me | H | H | H | H | 73–77 |

TABLE 3-continued

| cmpd. No. | R₁ | R₂ | R₃ | R₄ | R₅ | R₆ | R₇ | R₈ | phys. data m.p. °C. |
|---|---|---|---|---|---|---|---|---|---|
| 3.7 | 6-Br | H | n-propyl | Me | H | H | H | H | 113–116 |
| 3.8 | 6-I | H | n-propyl | Me | H | H | H | H | |
| 3.9 | 6-Cl | H | n-butyl | Me | H | H | H | H | |
| 3.10 | 6-Br | H | n-butyl | Me | H | H | H | H | |
| 3.11 | 6-I | H | n-butyl | Me | H | H | H | H | |
| 3.12 | 6-Cl | H | i-butyl | Me | H | H | H | H | |
| 3.13 | 6-Br | H | i-butyl | Me | H | H | H | H | |
| 3.14 | 6-Cl | H | cyclo-propyl-CH₂ | Me | H | H | H | H | |
| 3.15 | 6-Br | H | cyclo-propyl-CH₂ | Me | H | H | H | H | |
| 3.16 | 6-Cl | H | Me | H | Me | H | H | H | |
| 3.17 | 6-Br | H | Me | H | Me | H | H | H | |
| 3.18 | 6-I | H | Me | H | Me | H | H | H | |
| 3.19 | 6-Cl | H | Et | H | Me | H | H | H | |
| 3.20 | 6-Br | H | Et | H | Me | H | H | H | |
| 3.21 | 6-Cl | H | n-propyl | H | Me | H | H | H | 66–68 |
| 3.22 | 6-Br | H | n-propyl | H | Me | H | H | H | 64–66 |
| 3.23 | 6-I | H | n-propyl | H | Me | H | H | H | |
| 3.24 | 6-Cl | H | n-butyl | H | Me | H | H | H | |
| 3.25 | 6-Br | H | n-butyl | H | Me | H | H | H | |
| 3.26 | 6-I | H | n-butyl | H | Me | H | H | H | |
| 3.27 | 6-Cl | H | i-butyl | H | Me | H | H | H | |
| 3.28 | 6-Br | H | i-butyl | H | Me | H | H | H | |
| 3.29 | 6-Cl | H | cyclo-propyl-CH₂ | H | Me | H | H | H | |
| 3.30 | 6-Br | H | cyclo-propyl-CH₂ | H | Me | H | H | H | |
| 3.31 | 6-Cl | H | Me | H | Cl | Cl | H | H | |
| 3.32 | 6-Br | H | Me | H | Cl | Cl | H | H | |
| 3.33 | 6-I | H | Me | H | Cl | Cl | H | H | |
| 3.34 | 6-Cl | H | Et | H | Cl | Cl | H | H | |
| 3.35 | 6-Br | H | Et | H | Cl | Cl | H | H | |
| 3.36 | 6-Cl | H | n-propyl | H | Cl | Cl | H | H | 94–96 |
| 3.37 | 6-Br | H | n-propyl | H | Cl | Cl | H | H | |
| 3.38 | 6-I | H | n-propyl | H | Cl | Cl | H | H | |
| 3.39 | 6-Cl | H | n-butyl | H | Cl | Cl | H | H | |
| 3.40 | 6-Br | H | n-butyl | H | Cl | Cl | H | H | |
| 3.41 | 6-I | H | n-butyl | H | Cl | Cl | H | H | |
| 3.42 | 6-Cl | H | i-butyl | H | Cl | Cl | H | H | |
| 3.43 | 6-Br | H | i-butyl | H | Cl | Cl | H | H | |
| 3.44 | 6-Cl | H | cyclo-propyl-CH₂ | H | Cl | Cl | H | H | |
| 3.45 | 6-Br | H | cyclo-propyl-CH₂ | H | Cl | Cl | H | H | |
| 3.46 | 6-Cl | H | Me | H | F | F | H | H | |
| 3.47 | 6-Br | H | Me | H | F | F | H | H | |
| 3.48 | 6-I | H | Me | H | F | F | H | H | |
| 3.49 | 6-Cl | H | Et | H | F | F | H | H | |
| 3.50 | 6-Br | H | Et | H | F | F | H | H | |
| 3.51 | 6-Cl | H | n-propyl | H | F | F | H | H | Oil, ¹H-NMR |
| 3.52 | 6-Br | H | n-propyl | H | F | F | H | H | Oil, ¹H-NMR |
| 3.53 | 6-I | H | n-propyl | H | F | F | H | H | |
| 3.54 | 6-Cl | H | n-butyl | H | F | F | H | H | |
| 3.55 | 6-Br | H | n-butyl | H | F | F | H | H | |
| 3.56 | 6-I | H | n-butyl | H | F | F | H | H | |
| 3.57 | 6-Cl | H | i-butyl | H | F | F | H | H | |
| 3.58 | 6-Br | H | i-butyl | H | F | F | H | H | |
| 3.59 | 6-Cl | H | cyclo-propyl-CH₂ | H | F | F | H | H | |
| 3.60 | 6-Br | H | cyclo-propyl-CH₂ | H | F | F | H | H | |
| 3.61 | 6-Cl | H | n-propyl | H | Me | Me | H | H | |
| 3.62 | 6-Br | H | n-propyl | H | Me | Me | H | H | |
| 3.63 | 6-Cl | H | n-butyl | H | Me | Me | H | H | |
| 3.64 | 6-Br | H | n-butyl | H | Me | Me | H | H | |
| 3.65 | 6-Cl | H | n-propyl | H | Me | H | Me | H | |
| 3.66 | 6-Br | H | n-propyl | H | Me | H | Me | H | |
| 3.67 | 6-Cl | H | n-butyl | H | Me | H | Me | H | |
| 3.68 | 6-Br | H | n-butyl | H | Me | H | Me | H | |
| 3.69 | 6-Br | H | n-propyl | H | CF₃ | H | H | H | |
| 3.70 | 6-Cl | H | n-propyl | H | CF₃ | H | H | H | |

TABLE 4

| cmpd. No. | R₁ | R₂ | R₃ | R₄ | R₅ | R₆ | R₇ | R₈ | phys. data m.p. °C. |
|---|---|---|---|---|---|---|---|---|---|
| 4.1 | H | 6-Cl | Me | Me | H | H | H | H | |
| 4.2 | H | 6-Br | Me | Me | H | H | H | H | |
| 4.3 | 7-Br | H | Me | Me | H | H | H | H | |
| 4.4 | H | 6-Cl | Et | Me | H | H | H | H | |
| 4.5 | 7-Br | H | Et | Me | H | H | H | H | |
| 4.6 | H | 6-Cl | n-propyl | Me | H | H | H | H | |
| 4.7 | H | 6-Br | n-propyl | Me | H | H | H | H | |
| 4.8 | 7-Br | H | n-propyl | Me | H | H | H | H | 100–103 |
| 4.9 | H | 6-Cl | n-butyl | Me | H | H | H | H | |
| 4.10 | H | 6-Br | n-butyl | Me | H | H | H | H | |
| 4.11 | 7-Br | H | n-butyl | Me | H | H | H | H | |
| 4.12 | H | 6-Cl | i-butyl | Me | H | H | H | H | |
| 4.13 | 7-Br | H | i-butyl | Me | H | H | H | H | |
| 4.14 | H | 6-Cl | cyclo-propyl-CH₂ | Me | H | H | H | H | |
| 4.15 | 7-Br | H | cyclo-propyl-CH₂ | Me | H | H | H | H | |
| 4.16 | H | 6-Cl | Me | H | Me | H | H | H | |
| 4.17 | H | 6-Br | Me | H | Me | H | H | H | |
| 4.18 | 7-Br | H | Me | H | Me | H | H | H | |
| 4.19 | H | 6-Cl | Et | H | Me | H | H | H | |
| 4.20 | 7-Br | H | Et | H | Me | H | H | H | |
| 4.21 | H | 6-Cl | n-propyl | H | Me | H | H | H | |
| 4.22 | H | 6-Br | n-propyl | H | Me | H | H | H | |

TABLE 4-continued

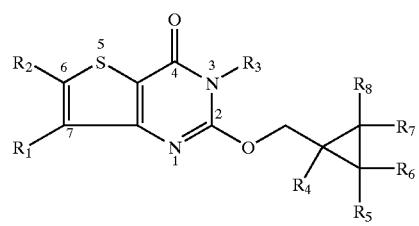

| cmpd. No. | $R_1$ | $R_2$ | $R_3$ | $R_4$ | $R_5$ | $R_6$ | $R_7$ | $R_8$ | phys. data m.p. °C. |
|---|---|---|---|---|---|---|---|---|---|
| 4.23 | 7-Br | H | n-propyl | H | Me | H | H | H | 112–115 |
| 4.24 | H | 6-Cl | n-butyl | H | Me | H | H | H | |
| 4.25 | H | 6-Br | n-butyl | H | Me | H | H | H | |
| 4.26 | 7-Br | H | n-butyl | H | Me | H | H | H | |
| 4.27 | H | 6-Cl | i-butyl | H | Me | H | H | H | |
| 4.28 | 7-Br | H | i-butyl | H | Me | H | H | H | |
| 4.29 | H | 6-Cl | cyclo-propyl-$CH_2$ | H | Me | H | H | H | |
| 4.30 | 7-Br | H | cyclo-propyl-$CH_2$ | H | Me | H | H | H | |
| 4.31 | H | 6-Cl | Me | H | Cl | Cl | H | H | |
| 4.32 | H | 6-Br | Me | H | Cl | Cl | H | H | |
| 4.33 | 7-Br | H | Me | H | Cl | Cl | H | H | |
| 4.34 | H | 6-Cl | Et | H | Cl | Cl | H | H | |
| 4.35 | 7-Br | H | Et | H | Cl | Cl | H | H | |
| 4.36 | H | 6-Cl | n-propyl | H | Cl | Cl | H | H | |
| 4.37 | H | 6-Br | n-propyl | H | Cl | Cl | H | H | |
| 4.38 | 7-Br | H | n-propyl | H | Cl | Cl | H | H | |
| 4.39 | H | 6-Cl | n-butyl | H | Cl | Cl | H | H | |
| 4.40 | H | 6-Br | n-butyl | H | Cl | Cl | H | H | |
| 4.41 | 7-Br | H | n-butyl | H | Cl | Cl | H | H | |
| 4.42 | H | 6-Cl | i-butyl | H | Cl | Cl | H | H | |
| 4.43 | 7-Br | H | i-butyl | H | Cl | Cl | H | H | |
| 4.44 | H | 6-Cl | cyclo-propyl-$CH_2$ | H | Cl | Cl | H | H | |
| 4.45 | 7-Br | H | cyclo-propyl-$CH_2$ | H | Cl | Cl | H | H | |
| 4.46 | H | 6-Cl | Me | H | F | F | H | H | |
| 4.47 | H | 6-Br | Me | H | F | F | H | H | |
| 4.48 | 7-Br | H | Me | H | F | F | H | H | |
| 4.49 | H | 6-Cl | Et | H | F | F | H | H | |
| 4.50 | 7-Br | H | Et | H | F | F | H | H | |
| 4.51 | H | 6-Cl | n-propyl | H | F | F | H | H | |
| 4.52 | H | 6-Br | n-propyl | H | F | F | H | H | |
| 4.53 | 7-Br | H | n-propyl | H | F | F | H | H | |
| 4.54 | H | 6-Cl | n-butyl | H | F | F | H | H | |
| 4.55 | H | 6-Br | n-butyl | H | F | F | H | H | |
| 4.56 | 7-Br | H | n-butyl | H | F | F | H | H | |
| 4.57 | H | 6-Cl | i-butyl | H | F | F | H | H | |
| 4.58 | 7-Br | H | i-butyl | H | F | F | H | H | |
| 4.59 | H | 6-Cl | cyclo-propyl-$CH_2$ | H | F | F | H | H | |
| 4.60 | 7-Br | H | cyclo-propyl-$CH_2$ | H | F | F | H | H | |
| 4.61 | H | 6-Cl | n-propyl | H | Me | Me | H | H | |
| 4.62 | 7-Br | H | n-propyl | H | Me | Me | H | H | |
| 4.63 | H | 6-Cl | n-butyl | H | Me | Me | H | H | |
| 4.64 | 7-Br | H | n-butyl | H | Me | Me | H | H | |
| 4.65 | H | 6-Cl | n-propyl | H | Me | H | Me | H | |
| 4.66 | 7-Br | H | n-propyl | H | Me | H | Me | H | |
| 4.67 | H | 6-Cl | n-butyl | H | Me | H | Me | H | |
| 4.68 | 7-Br | H | n-butyl | H | Me | H | Me | H | |
| 4.69 | H | 6-Cl | n-propyl | H | $CF_3$ | H | H | H | |
| 4.70 | 7-Br | H | n-propyl | H | $CF_3$ | H | H | H | |

Examples for specific formulatons-combination are as disclosed e.g. in WO 97/33890, e.g. for wettable powders, emulsifiable concentrates, dusts, extruder granules, coated granules, solutions and suspension concentrates.

BIOLOGICAL EXAMPLES

Fungicidal Actions

B-1

Action Against *Puccinia graminis* on Wheat a) Residual-protective Action 6 days after sowing, wheat plants are sprayed to drip point with an aqueous spray mixture (0.02% active ingredient) prepared from a wettable powder formulation of the test compound and infected 24 hours later with a uredospore suspension of the fungus. After an incubation time of 48 hours (conditions: 95 to 100% relative humidity at 20° C.), the plants are stood at 22° C. in a greenhouse. Evaluation of fungal infestation is made 12 days after infection.

b) Systemic Action

Wheat plants are drenched 5 days after sowing with an aqueous spray mixture (0.006% a.i., based on the volume of the soil) prepared from a wettable powder formulation of the test compound. Care is taken that the spray mixture does not come into contact with the growing parts of the plants. After 48 hours, the plants are infected with a uredospore suspension of the fungus. After an incubation period of 48 hours (conditions: 95 to 100% relative humidity at 20° C.), the plants are stood at 22° C. in a greenhouse. Evaluation of the fugal infestation is made 12 days after infection.

Compounds of Tables 1–4 show good to excellent activity, preferably the compounds 1.7, 1.10, 1.15, 1.22, 1.25, 1.30, 1.37, 3.6, ,3.7, 3.21, 3.22, 3.36, 3.51, 3.52, 4.8 and 4.23.

Example B-2

Action Against *Colletotrichum lagenarium* on Cucumbers

After a growth period of 2 weeks, cucumber plants are sprayed with an aqueous spray mixture (concentration 0.002%) prepared from a wettable powder formulation of the test compound and infected 2 days later with a spore suspension (1.5×10⁵ spores/ml) of the fungus and incubated for 36 hours at 23° C. and high humidity. Incubation is then continued at normal humidity and c. 22° C. Evaluation of the fungal infestation is made 8 days after infection.

The compounds of the Tables 1–4 show good to excellent activity, preferably the compounds 1.7, 1.10, 1.15, 1.22, 1.25, 1.30, 1.37, 3.6, 3.7, 3.21, 3.22, 3.36, 3.51, 3.52, 4.8 and 4.23.

Example B-3

Residual-protective Action Against *Venturia inaegualis* on Apples

Apple cuttings with fresh shoots 10 to 20 cm long are sprayed to drip point with a spray mixture (0.02% a.i.) prepared from a wettable powder formulation of the test compound. The plants are infected 24 hours later with a conidia suspension of the fungus. The plants are then incubated for 5 days at 90 to 100% relative humidity and stood in a greenhouse for a further 10 days at 20 to 24° C. Evaluation of the fungal infestation is made 12 days after infection.

Compounds of Tables 1–4 show good activity, preferably the compounds 1.7, 1.10, 1.15, 1.22, 1.25, 1.30, 1.37, 3.6, 3.7, 3.21, 3.22, 3.36, 3.51, 3.52, 4.8 and 4.23.

Example B-4

Action Against *Erysiphe graminis* on Barley a) Residual-protective Action

Barley plants about 8 cm in height are sprayed to drip point with a spray mixture (0.02% a.i.) prepared from a wettable powder formulation of the test compound, and the treated plants are dusted with conidia of the fungus 3 to 4 hours later. The infected plants are stood in a greenhouse at 220° C. Evaluation of the fungal infection is made 12 days after infection.

b) Systemic Action

Barley plants about 8 cm in height are drenched with an aqueous spray mixture (0.002% a.i., based on the volume of the soil):prepared from a wettable powder formulation of the test compound. Care is taken that the spray mixture does not come into contact with the growing parts of the plants. The treated plants are dusted 48 hours later with conidia of the fungus. The infected plants are then stood in a greenhouse at 22° C. Evaluation of the fungal infestation is made 12 days after infection.

Compared with the control plants, infestation of the plants treated with compounds of formula I, for example the compounds 1.7, 1.10, 1.15, 1.22, 1.25, 1.30, 1.37, 3.6, 3.7, 3.21, 3.22 and 3.36, is 20% or less.

Example B-5

Action Against *Podosphaera leucotricha* on Apple Shoots

Apple cuttings with fresh shoots about 15cm long are sprayed with a spray mixture (0.06% a.i.). The plants are infected 24 hours later with a conidia suspension of the fungus and stood in a climatic chamber at 70% relative humidity and 200° C. Evaluation of the fugal infestation is made 12 days after infection.

Compounds of Tables 1–4 show good activity. The following compounds exhibit especially strong efficacy: 1.7, 1.10, 1.15, 1.22, 1.25, 1.30, 1.37, 3.6, 3.7, 3.21, 3.22 and 3.36 (0–5% infestation).

Example B-6

Action Against *Uncinula necator* on Vines 5 week old vine cuttings are sprayed with a spray mixture (200 ppm a.i.) prepared from a wettable powder formulation of the test compound. The plants are infected 24 hours later by conidias from strongly infested vine leafs that are shaken off over the test plants. The plants are then incubated at 26° C. and 60% relative humidity. The evaluation of the fungal infestation is made ca. 14 days after infection.

Compared with the control plants, infestation of the plants treated with compounds of formula I, for example the compounds 1.7, 1.10, 1.15, 1.22, 1.25, 1.30, 1.37, 3.6, 3.7, 3.21, 3.22 and 3.36, is 20% or less.

What is claimed is:

1. A compound of formula I

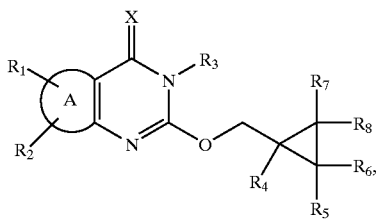

I wherein

A is phenyl, thienyl (including all 3 isomers), thiazolyl or pyridyl;

X is oxygen or sulfur;

$R_1$ is hydrogen, halogen or trimethylsilyl;

$R_2$ is hydrogen, halogen or trimethylsilyl; and at least one of $R_1$ and $R_2$ is not hydrogen;

$R_3$ is $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, —(CH$_2$)$_n$—$C_3$–$C_8$cycloalkyl which are unsubstituted or substituted by halogen, $C_1$–$C_6$alkyl or $C_1$–$C_6$haloalkyl; $C_1$–$C_4$alkoxy-$C_1$–$C_6$alkyl; $C_1$–$C_4$alkoxy-$C_2$–$C_6$alkenyl; $C_1$–$C_4$alkoxy-$C_2$–$C_6$alkynyl; $C_1$–$C_4$alkylthio-$C_1$–$C_6$alkyl; $C_1$–$C_4$alkylthio-$C_2$–$C_6$alkenyl; $C_1$–$C_4$alkylthio-$C_2$–$C_6$alkynyl; mono-$C_1$–$C_4$alkylamin-$C_3$–$C_6$alkyl; mono-$C_1$–$C_4$alkylamin-$C_2$–$C_6$alkenyl; mono-$C_1$–$C_4$alkylamin-$C_2$–$C_6$alkynyl; —(CH$_2$)$_n$—$C_1$–$C_4$alkoxy-$C_3$–$C_6$cycloalkyl; —(CH$_2$)$_n$—$C_1$–$C_4$alkythio-$C_3$–$C_6$cycloalkyl; —(CH$_2$)$_n$—mono-$C_1$–$C_4$alkylamin-$C_3$–$C_6$cycloalkyl; or N=CR$_9$R$_{10}$;

n is 1, 2, 3 or 4;

$R_4$, $R_5$, $R_6$, $R_7$ and $R_8$ are each independently of the other hydrogen, $C_1$–$C_4$alkyl, $C_1$–$C_4$haloalkyl or halogen, wherein at least one of the substituents $R_4$–$R_8$ must be different from hydrogen; and $R_9$ is hydrogen, $C_1$–$C_6$alkyl, $C_3$–$C_7$cycloalkyl, pyridyl, furyl, thienyl or phenyl which is unsubstituted or mono to pentasubstituted by halogen, $C_1$–$C_6$alkyl, $C_1$–$C_6$haloalkyl, $C_1$–$C_6$alkoxy or $C_1$–$C_6$haloalkoxy;

$R_{10}$ is hydrogen, $C_1$–$C_6$alkyl, $C_3$–$C_7$cycloalkyl, pyridyl, furyl, thienyl or phenyl which is unsubstituted or mono to pentasubstituted by halogen, $C_1$–$C_6$alkyl, $C_1$–$C_6$haloalkyl, $C_1$–$C_6$alkoxy or $C_1$–$C_6$haloalkoxy; and at least one of $R_9$ and $R_{10}$ is not hydrogen.

2. A compound of formula I according to claim 1, wherein A is thienyl, and X is oxygen.

3. A compound of formula I according to claim 2, wherein $R_1$ is hydrogen, fluorine, chlorine, bromine or iodine;

$R_2$ is hydrogen, fluorine, chlorine, bromine or iodine; and at least one of $R_1$ and $R_2$ is not hydrogen;

$R_3$ is $C_1$–$C_4$alkyl, $C_2$–$C_4$alkenyl, $C_2$–$C_4$alkynyl, $C_1$–$C_4$haloalkyl, $C_2$–$C_4$haloal $C_2$–$C_4$haloalkynyl or CH$_2$—$C_3$–$C_4$cycloalkyl which are unsubstituted or substituted by halogen, $C_1$–$C_4$alkyl or $C_1$–$C_4$haloalkyl;

$R_4$, $R_5$, $R_6$, $R_7$ and $R_8$ are each independently of the other hydrogen, fluorine, chlorine, bromine, iodine, $C_1$–$C_4$alkyl or $C_1$–$C_4$haloalkyl, wherein at least one of the substituents $R_4$–$R_8$ must be different from hydrogen.

4. A compound of formula I according to claim 3, wherein $R_3$ is $C_1$–$C_4$alkyl, $C_2$–$C_4$alkenyl, $C_2$–$C_4$alkynyl each of which is unsubstituted or substituted by chlorine or bromine; or CH$_2$—$C_3$–$C_4$cycloalkyl, :which is unsubstituted or substituted by fluorine, chlorine, bromine or iodine;

$R_4$, $R_5$, $R_6$, $R_7$ and $R_8$ are each independently of the other hydrogen, fluorine, chlorine, bromine, iodine, $C_1$–$C_4$alkyl or $C_1$–$C_2$haloalkyl, wherein at least one of the substituents $R_4$–$R_8$ must be different from hydrogen.

5. A compound of formula I according to claim 4, wherein $R_1$ is hydrogen, chlorine or bromine;

$R_2$ is hydrogen, chlorine or bromine; and at least one of $R_1$ and $R_2$ is not hydrogen;

$R_3$ is $C_1$–$C_4$alkyl or CH$_2$-cyclopropyl;

$R_4$, $R_5$, $R_6$, $R_7$ and $R_8$ are each independently of the other hydrogen, chlorine, bromine, iodine, $C_1$–$C_4$alkyl or $C_1$–$C_2$haloalkyl, wherein at least one of the substituents $R_4$–$R_8$ must be different from hydrogen.

6. A compound of formula I according to claim 5, wherein
A is thienyl[2.3-d],
$R_3$ is $C_3$–$C_4$alkyl,
$R_4$, $R_5$, $R_6$, $R_7$ and $R_8$ are each independently of the other hydrogen, chlorine, bromine, methyl or $CF_3$, wherein at least one of the substituents $R_4$–$R_8$ must be different from hydrogen.

7. A compound of formula I according to claim 5, wherein
A is thienyl[3.2-d],
$R_3$ is $C_3$–$C_4$alkyl,
$R_4$, $R_5$, $R_6$, $R_7$ and $R_8$ are each independently of the other hydrogen, chlorine, bromine, methyl or $CF_3$, wherein at least one of the substituents $R_4$–$R_8$ must be different from hydrogen.

8. A compound according to claim 1, selected from
6-bromo-2-(1-methylcyclopropylmethoxy)-3-n-propyl-3Hquinazoline4-one,
6-bromo-2-(2-methylcyclopropylmethoxy)-3-n-propyl-3H-quinazoline-4-one,
6-bromo-2-(1-methylcyclopropylmethoxy)-3-n-buyl-3H-quinazoline-4-one,
6-bromo-2-(2-methylcyclopropylmethoxy)-3-n-buyl-3H-quinazoline-4-one,
6-bromo-2-(1-methylcyclopropylmethoxy)-3-n-propyl-3H-thieno[2.3-d]pyrimidin-4-one,
6-chloro-2-(1-methylcyclopropylmethoxy)-3-n-propyl-3H-thieno[2.3-d]pyrimidin-4-one,
6-bromo-2-(2-methylcyclopropylmethoxy)-3-n-propyl-3H-thieno[2.3-d]pyrimidin-4-one,
6-chloro-2-(2-methylcyclopropyimethoxy)-3-n-propyl-3H-thieno[2.3-d]pyrimidin-4-one,
6-bromo-2-(1-methylcyclopropylmethoxy)-3-n-buyl-3H-thieno[2.3-d]pyrimidin-4-one,
6-chloro-2-(1-methyicyclopropylmethoxy)-3-n-buyl-3H-thieno[2.3-d]pyrimidin-4-one,
6-bromo-2-(2-methylcyclopropylmethoxy)-3-n-buyl-3H-thieno[2.3-d]pyrimidin-4-one,
6-chloro-2-(2-methylcyclopropylmethoxy)-3-n-buyl-3H-thieno[2.3-d]pyrimidin-4-one.

9. A composition for controlling and preventing phytopathogenic microorganisms, wherein the active ingredient is a compound as claimed in claim 1 together with a suitable carrier.

10. A method of controlling or preventing infestation of cultivated plants by phytopathogenic fungi by application of a compound of formula I as claimed in claim 1 to plants, to parts thereof or to the locus thereof.

11. A method for the preparation of a compound of formula I according to claim 1, which comprises
a) converting an α-amino-β-carboalkoxyheterocycle of formula II, wherein $R_1$ and $R_2$ have the meanings stated for formula I and R is $C_1$–$C_6$alkyl,

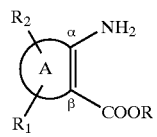

II with thiophosgene in an alkaline medium and in the presence of a solvent into an isothiocyanate of formula III

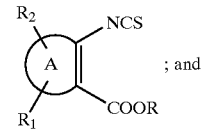

III

; and b) treating the isothiocyanate with an amine of formula $NH_2R_3$, wherein $R_3$ has the meaning stated for formula I, in the presence of a solvent and if necessary in the presence of a base, and obtaining, with ring closure, the 2-thioxopyrimidin-4-one derivative of formula V

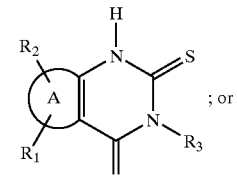

V

; or c) treating the amine of formula II with an 1-isocyanatoalkane in the presence of a solvent (alcohol or dimethylformamid) obtaining thioureidothiophenes of formula IV.

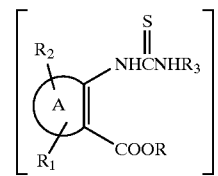

IV

12. A compound of formula IV

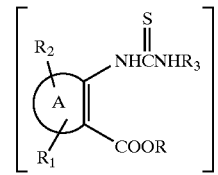

IV wherein
A is thienyl[2.3-d] or thienyl[3.2-d];
$R_1$ is hydrogen, halogen or trimethylsilyl;
$R_2$ is hydrogen, halogen or trimethylsilyl; and at least one of $R_1$ and $R_2$ is not hydrogen;
$R_3$ is $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl or $CH_2$—$C_3$–$C_6$cycloalkyl which are unsubstituted or substituted by halogen, $C_1$–$C_6$alkyl or $C_1$–$C_6$haloalkyl;
$R_4$, $R_5$, $R_6$, $R_7$ and $R_8$ are each independently of the other hydrogen, $C_1$–$C_4$alkyl, $C_1$–$C_4$haloalkyl or halogen, wherein at least one of the substituents $R_4$–$R_8$ must be different from hydrogen; and
R is hydrogen or $C_1$–$C_6$alkyl.

* * * * *